(12) United States Patent
Podszuweit et al.

(10) Patent No.: US 8,343,405 B2
(45) Date of Patent: Jan. 1, 2013

(54) METHOD FOR PRODUCING A TRANSPARENT BODY THAT INCORPORATES AN OBJECT

(75) Inventors: Dietmar Podszuweit, Hamburg (DE); Manfred Martens, Hamburg (DE); Holger Wuttke, Hamburg (DE)

(73) Assignee: Montblanc-Simplo GmbH (DE)

( * ) Notice: Subject to any disclaimer, the term of this patent is extended or adjusted under 35 U.S.C. 154(b) by 1294 days.

(21) Appl. No.: 12/083,907

(22) PCT Filed: Sep. 18, 2006

(86) PCT No.: PCT/EP2006/009064
§ 371 (c)(1),
(2), (4) Date: Apr. 17, 2008

(87) PCT Pub. No.: WO2007/045316
PCT Pub. Date: Apr. 26, 2007

(65) Prior Publication Data
US 2009/0249608 A1     Oct. 8, 2009

(30) Foreign Application Priority Data
Oct. 20, 2005    (DE) ...................... 10 2005 050 320

(51) Int. Cl.
*B29C 47/76*    (2006.01)
*B29C 65/00*    (2006.01)
*B23K 37/00*    (2006.01)
*A47G 1/12*     (2006.01)

(52) U.S. Cl. ........ 264/248; 264/101; 264/102; 264/249; 156/228; 156/286; 156/309.6; 156/349; 156/381; 156/382; 156/580; 428/13; 428/14; 428/542.2

(58) Field of Classification Search .................. 264/101, 264/102, 248, 249; 156/228, 286, 349, 381, 156/382, 580, 309.6; 428/13, 14, 542.2
See application file for complete search history.

(56) References Cited

U.S. PATENT DOCUMENTS

| | | | | |
|---|---|---|---|---|
| 2,379,793 A * | 7/1945 | Eenigenburg | ................ | 264/275 |
| 2,451,913 A * | 10/1948 | Brice | ............................. | 428/67 |
| 2,455,215 A | 11/1948 | Beckwith et al. | | |
| 2,867,053 A * | 1/1959 | Boor | .............................. | 312/31 |
| 3,596,317 A | 8/1971 | Nicholson | | |
| 4,078,962 A | 3/1978 | Krueger | | |
| 5,456,776 A * | 10/1995 | Noguchi | ........................ | 156/57 |
| 5,560,984 A * | 10/1996 | Tanimoto et al. | .......... | 428/300.7 |
| 5,662,970 A * | 9/1997 | Noguchi | ........................ | 428/24 |
| 6,060,011 A * | 5/2000 | Zandvliet et al. | ............ | 264/275 |

(Continued)

FOREIGN PATENT DOCUMENTS

DE        196 17 621 A1    11/1997

(Continued)

*Primary Examiner* — Christina Johnson
*Assistant Examiner* — Atul P Khare
(74) *Attorney, Agent, or Firm* — Lerner, David, Littenberg, Krumholz & Mentlik, LLP

(57) ABSTRACT

The invention relates to a production method for incorporating an object into a multi-part, transparent casing. According to the method, an object is aligned on a first joint surface of a first casing part and is pressed into said part using a second casing part with a second joint surface. The first joint surface of the first casing part and the second joint surface of the second casing part are then fused by pressure and temperature, forming a region between the casing parts that is devoid of a visible seam.

13 Claims, 5 Drawing Sheets

U.S. PATENT DOCUMENTS

| | | | |
|---|---|---|---|
| 6,522,549 B2 * | 2/2003 | Kano et al. | 361/737 |
| 6,649,009 B1 * | 11/2003 | Kim | 156/257 |
| 6,737,151 B1 * | 5/2004 | Smith | 428/192 |
| 6,743,327 B2 * | 6/2004 | Schober | 156/309.6 |
| 7,008,700 B1 * | 3/2006 | Goodson et al. | 428/542.2 |
| 7,481,957 B1 * | 1/2009 | Adickes | 264/261 |
| 7,550,057 B1 * | 6/2009 | Goodson et al. | 156/312 |
| 7,776,412 B1 * | 8/2010 | Adickes | 428/13 |
| 8,088,457 B2 * | 1/2012 | Adickes | 428/13 |
| 2003/0113485 A1 * | 6/2003 | Schober | 428/13 |
| 2003/0124296 A1 * | 7/2003 | Smith | 428/49 |
| 2004/0247801 A1 * | 12/2004 | Schober | 428/13 |
| 2005/0182167 A1 * | 8/2005 | Goodson et al. | 524/115 |
| 2006/0147655 A1 * | 7/2006 | Schober | 428/13 |

FOREIGN PATENT DOCUMENTS

| | | |
|---|---|---|
| FR | 2 637 532 A1 | 4/1990 |
| JP | 42148 | 1/1967 |
| JP | 44022629 Y1 | 9/1969 |
| JP | 4827839 | 4/1973 |
| JP | 2003-136598 A | 5/2003 |
| WO | WO-98/05385 A1 | 2/1998 |

* cited by examiner

METHOD FOR PRODUCING A TRANSPARENT BODY THAT INCORPORATES AN OBJECT

TECHNICAL FIELD

The present invention relates to a production method for incorporating an object in a multi-part transparent casing, as well as to a transparent body with an enclosed object.

BACKGROUND TO THE INVENTION

In the field of luxury articles, in order to improve the visual appearance of precious stones, optical effects, for example a magnifying glass effect or magnifying or diminution effects are frequently used. The basic principle of this consists of inserting and positioning an object in a transparent body or in a casing, and subsequently, by means of shaping such as lathe processing and/or polishing, to provide visual effects to the transparent casing.

In present-day methods for inserting an object in a transparent casing, the casing parts are fused on and an object is placed therein. However, positioning and alignment of the object in the casing is problematical because said object has to be held from the outside during the fusing process of the casing parts, and thus seams or scars arise that remain permanently visible.

PRESENTATION OF THE INVENTION

It is an object of the invention to provide a method for incorporating a three-dimensional object in a transparent casing.

According to an exemplary embodiment of the invention, a production method for incorporating an object in a multi-part casing that is at least in part transparent is provided. In the method according to the invention a first casing part with a first joint surface, and a second casing part with a second joint surface are provided. On or in the region of the first joint surface of the first casing part an object is aligned. The first casing part and the second casing part are then brought together so that the object remains, or is temporarily fixed by clamping, between the first joint surface and the second joint surface. If the object is aligned in a defined position on the first joint surface, a situation can be achieved in which said object remains in this defined position when the first casing part and the second casing part are brought together. The first joint surface of the first casing part is then fused to the second joint surface of the second casing part in that the first joint surface and the second joint surface are subjected to a pressure force and to a temperature so that the first casing part on the first joint surface makes a transition to the second casing part on the second joint surface devoid of a visible seam.

In a further exemplary embodiment a transparent body with an incorporated object is created, which body comprises a first casing part with a first joint surface, a second casing part with a second joint surface, and the object itself. In this arrangement the first joint surface of the first casing part can also be shaped such that the object can be positioned in a defined position on the first joint surface. The first joint surface of the first casing part and the second joint surface of the second casing part are joined such that a region between the casing parts is devoid of a visible seam.

With the present invention a production method is created by means of which any three-dimensional objects can be incorporated and aligned or positioned in a multi-part transparent casing, and by means of which production method no unsightly seams arise during the production process. In particular when setting precious stones, the angle of, view is extremely important, which angle can be predetermined by the precise positioning according to the invention. Subsequently, by means of this exact positioning of the three-dimensional objects, with the use of certain processing techniques, in particular lathe processing- and/or polishing techniques, a host of different visual effects can be created, for example magnification, diminution or distortion. Furthermore, the production method according to the invention is designed in a simple manner so that there is no need for the use of complicated control technologies or an expensive design. Below, the term "three-dimensional objects" refers to bodies whose height, width and thickness exceed approximately 0.1 cm. The term "seam" refers to a parting line of the respective casing parts between each other.

In a further exemplary embodiment of the production method the first casing part, the second casing part and the object are arranged in a guide funnel. To this effect, in a preceding process step, these three elements can, for example, be provisionally and temporarily interconnected to form a continuous formed body so that the object is temporarily fixed or jammed between the two joint surfaces. In this arrangement a connection can, for example, be achieved by means of a rim on one casing part which engages an associated elevation on the other casing part, as will be explained in more detail later on. By inserting in the guide funnel the continuous formed body that has been created in this way, a particular movement sequence during the joining process can be defined and predetermined. The guide funnel has a precisely defined clearance that matches the dimensions of the continuous formed body comprising the casing parts and the object so that this continuous formed body can be movably fitted in the guide funnel with great precision.

In a further exemplary embodiment of the method at least one plunger element moves into the guide funnel, and by this movement applies a pressure force to the first casing part and/or the second casing part. By means of the guide funnel and the plunger element it is thus possible to generate a defined pressure force that is aligned along the guide funnel in order to act on at least one of the two casing parts. It is thus possible to prevent any undesirable oblique application of force, which would, for example, displace the aligned object.

In a further exemplary embodiment of the method the object comprises a surface that is aligned at a right angle to a wall surface of the guide funnel. In this way the surface of the object is also aligned at a right angle in relation to the movement sequence in the guide funnel during the joining process, so that displacement of the aligned object can be prevented. In the case of precious stones or diamonds, this surface is also referred to as a "mirror".

In a further exemplary embodiment of the invention the plunger element generates the pressure force parallel in relation to the wall surface of the guide funnel. Displacement of the aligned object can thus be prevented so that no undesirable transverse forces arise.

In a further exemplary embodiment of the production method before or during fusing of the casing parts a vacuum is formed so that air inclusions can be prevented. In this way a clear or clear transparent casing can be provided without the view onto the pressed-in or welded-in object being impeded, for example, by air bubbles. Furthermore, the formation of a vacuum means that the required press force can be reduced so that in this case it is not necessary to compress trapped air voids. This also reduces the tension in the seam because there are no longer any pressurised air inclusions.

In a further exemplary embodiment the object is centred on the first joint surface of the first casing part, wherein the object is rotationally symmetrical in shape. With a centred object it is possible to achieve even distribution of force over the cross-sectional area of the seam so that no transverse forces occur which can displace the aligned object during the joining process.

In a further exemplary embodiment of the method the object is positioned in a volume-symmetrical manner in radial direction in relation to the first joint surface of the first casing part, and in relation to the second joint surface of the second casing part. In this way a situation is achieved in which no asymmetrical forces or transverse forces occur during the fusing process and during exertion of a pressure force, which asymmetrical forces or transverse forces would otherwise displace the precisely positioned object in an arbitrary direction. As a result of the same volume or the same mass of casing material being present around the object, no change in the position of the object can occur, for example in the case of pressure forces acting in a parallel manner.

In a further exemplary embodiment of the method an optical effect is achieved by means of processing, in particular by means of lathe processing and/or polishing a first casing surface of the first casing part, and/or of a second casing surface of the second casing part. In this context the term "casing surface" refers to the surface of the casing parts. By producing curved surfaces of the transparent casing any desired optical effects can be achieved that have a very interesting effect as far as the consumer is concerned. A magnification effect can, for example, make a precious stone appear more precious or larger. Analogously, diminution effects or distortion effects are imaginable.

In a further exemplary embodiment of the method the first casing part and the second casing part are produced by means of an injection moulding method. Above all where plastics or transparent plastics are used, the injection moulding method is particularly suitable for the production of the basic shapes or of the casing parts.

In a further exemplary embodiment at least one of the joint surfaces of the two casing parts is diamond polished so that the diamond-polished joint surface is smooth. The term "diamond polishing" refers to the production of a smooth surface, for example by means of diamond rotary-processing tools. In this way an extremely smooth surface structure is obtained, comparable to a surface that has been polished so that it is free of any grooves. With such a smooth surface, a clear and invisible seam can be produced.

In this context the term "smooth" refers to a roughness of less than $R_z=1$ μm. However, in order to prevent the seam from being visible from the outside, the transparency of the surface is at least as important as its smooth quality. Thus the surface should be a high-gloss surface rather than a matte surface.

In a further exemplary embodiment, at least one of the joint surfaces of the two casing parts is processed such that a high-gloss, mirror-finished, highly transparent surface is created. With this surface a seam can arise that does not produce reflections of any rough spots that may be present, so that said seam is invisible.

As already indicated earlier, in a further exemplary embodiment one of the two casing parts can comprise a rim that is circumferential at least in some sections, wherein the other casing part comprises an elevation.

The two casing parts can then be joined such that the rim engages the elevation having positive fit. The first casing part and the second casing part are thus connected in a stabilised manner having positive fit, wherein in the interior an object can be precisely positioned and affixed. In the subsequent joining process or during fusion the object can better be held in its aligned position.

In a further exemplary embodiment at least the rim of the first casing part or second casing part and/or the elevation of the first casing part or second casing part are/is conical. In this way a press fit or a form closure can be formed which lets the first and the second casing parts remain in their brought-together position, and thus ensures easier handling of the casing bodies and more accurate positioning.

In a further exemplary embodiment, the rim of the first or second casing part comprises openings in order to make it possible for air to escape. It is thus possible, during the press procedure, for air that has been trapped in the interior of the casing parts to escape so that no air bubbles can form during fusion, and so that a clear transparent material quality can be achieved.

In a further exemplary embodiment of the method, alignment of the object takes place in that, by means of a positioning form that approximately images the object in order to position said object therein, the object is centred in the first casing part or the second casing part. For example, if the object rests against the first joint surface of the first casing part, by means of the positioning form for example in the second joint surface, while the casing parts move towards each other, the object can move into the positioning form and can align itself. As an alternative it is also possible to place the object in the positioning form formed in the first casing part, and to temporarily affix the object in this position in that the joint surface of the second casing part is made to approach the object until it comes to rest against the object so as to securely jam the object in its position.

In a further exemplary embodiment of the method, during the step of fusing, the first casing part and the second casing part are heated up such that they assume a dough-like state. The term "dough-like state" refers to the usually viscous transition region between a solid and a liquid aggregate state of a medium. With the method according to the invention it is not absolutely necessary to create a fused state in which the compounds to be jointed have to assume a liquid state. Since the guide funnel is very precisely matched to the dimensions of the two casing parts, and since the material can thus not escape or flow out, it is possible, by application of pressure, to bring about a dough-like state, by means of which the two casing parts can be fused together. By means of this dough-like state the object can be held in the defined position, and drifting away from the defined position in an arbitrary direction can be prevented.

In a further exemplary embodiment of the transparent body, said transparent body further comprises a fastening element for being fastened to a retaining element. In this arrangement the retaining element can be selected from the group comprising fountain pens, pens, watches and jewelry.

In a further exemplary embodiment of the transparent body, said transparent body is produced according to the above-described exemplary embodiment of the production method according to the invention.

In an exemplary embodiment of the method, during fusing, a temperature of 120° C. to 160° C., preferably approximately 140° C., is selected. In this method the temperature should be maintained for a period of time of 1 to 5 seconds, preferably 3 seconds. In this method the plunger elements subject the casing parts that are to be joined to pressure ranging from 180 to 260 bar, preferably approximately 230 bar. During cooling the pressure is maintained at approximately 90° C. until the material of the casing parts has reached a solid state. The pressure that exists during the joining process until the fusing temperature has been reached can be 60 to 80 bar, preferably approximately 70 bar. Preferably plastic, for example Plexiglas 7H transparent or PMMA, is used for the casing parts. Other temperature ranges, pressure ranges or time periods can of course be advantageous if different materials are used.

BRIEF DESCRIPTION OF THE DRAWINGS

Below, for further explanation and to provide a better understanding of the present invention, various exemplary embodiments are described in more detail with reference to the enclosed drawings. The following are shown.

Identical or similar components in different figures have the same or corresponding reference characters.

The illustrations in the figures are diagrammatic and not to scale, however, they may show qualitative ratios of dimensions.

DETAILED DESCRIPTION OF EXEMPLARY EMBODIMENTS

Figure 1:
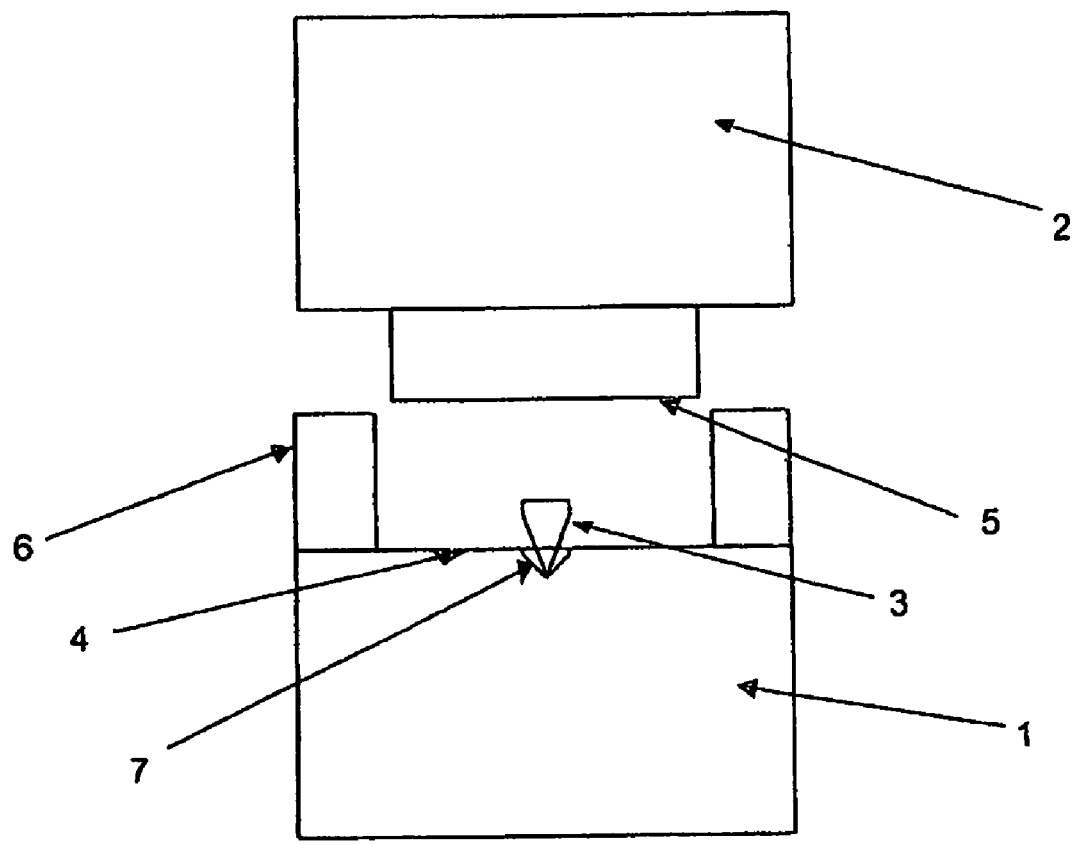
FIG. 1 a diagrammatic view of an exemplary embodiment of the production method according to the invention.

FIG. 1 shows an exemplary arrangement of the production method according to the invention for incorporating an object in a multi-part transparent casing. In this arrangement an object 3 can be aligned on a first joint surface 4 of a first casing part 1, and can be affixed and enclosed by means of bringing the first casing part together with a second casing part 2. Subsequently, the first joint surface 4 of the first casing part 1 and the second joint surface 5 of the second casing part 2 can be fused by means of the application of pressure force and temperature so that a region between the casing parts 1, 2 is devoid of a visible seam. In this process the joint surfaces can preferably be produced and aligned so as to be plane-parallel.

Below, an exemplary arrangement for implementing the method according to the invention is described in detail with reference to FIG. 1. On a lower, transparent casing part 1 with a joint surface 4, an object 3 to be incorporated can be placed in a positioning form 7 and can be aligned as a result of the position and form of the positioning form 7. Subsequently, a second, upper, transparent casing part 2 can be made to engage the lower casing part 1. In this arrangement on the second, upper, transparent casing part 1 an elevation with a joint surface 5 is created. The elevation 5 can now be made to engage a rim 6 of the first casing part 1, as a result of which the casing parts 1, 2 and the object 3 unite to form a continuous formed body. In this way the object 3 can be positioned and fixed prior to the fusing process. After the object 3 has been temporarily fixed, under the influence of a pressure force a certain temperature is generated in a guide funnel (see FIG. 2), for example in the case of plastic a temperature between 120° C. and 160° C., which temperature makes it possible for the joint surfaces 4 and 5 or the upper casing part 2 and the lower casing part 1 to be fused or joined.

In this process the temperature can, for example, be maintained for three seconds and can drop to 90° C. while the same pressure is maintained, until such time as the material has solidified again.

In this way a single-part object is created which, while originally comprising several parts, nonetheless has the appearance of a single body in which an object is contained.

For example, Plexiglas 7H transparent or PMMA (polymethylmethacrylate) can be used. A preferred softening temperature can, for example, be 140° C. In a preferred embodiment of the method the rams can generate a pressure of 230 bar in the guide funnel.

Figure 2:
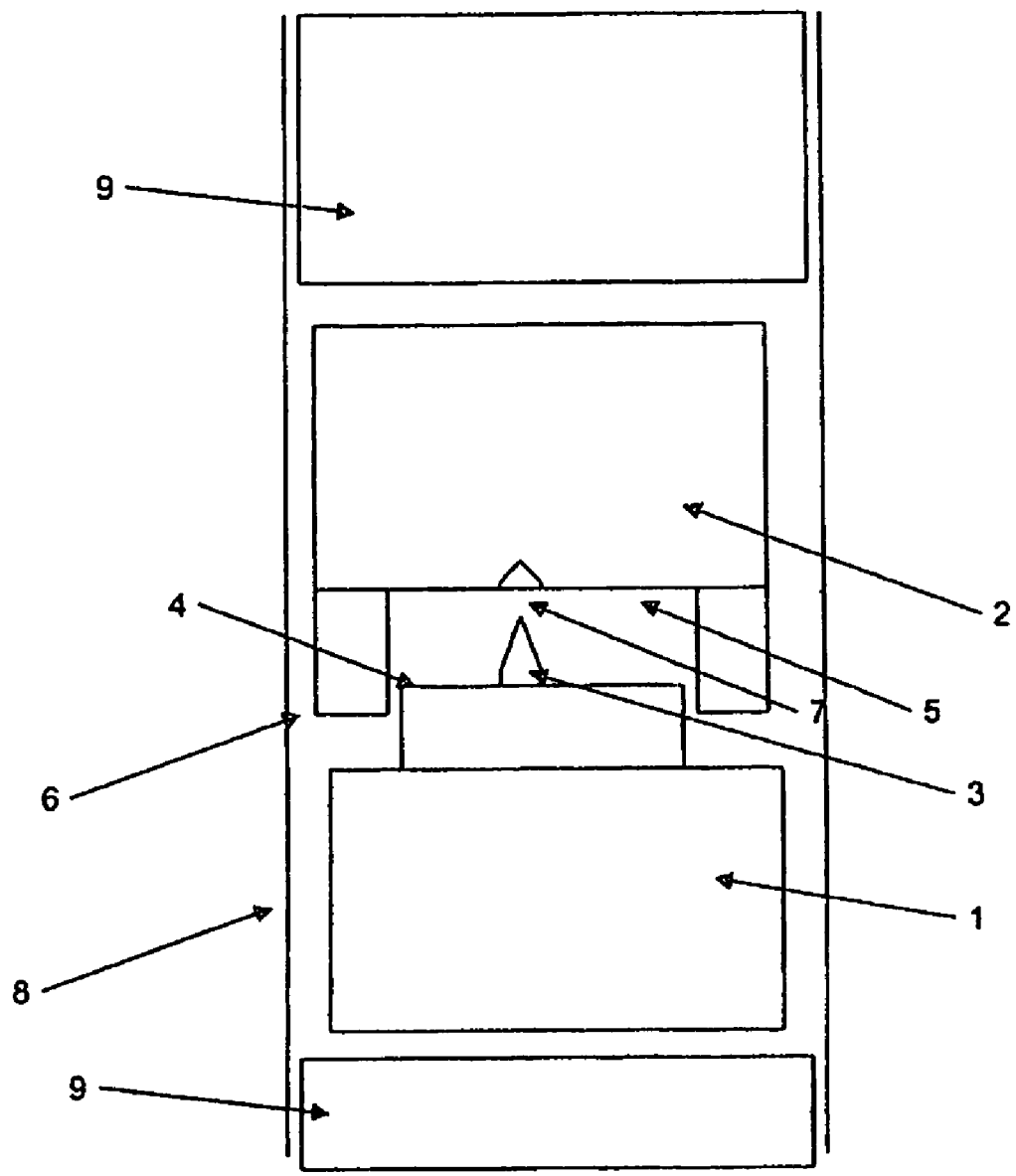
FIG. 2 a further diagrammatic view of an exemplary embodiment of the method.

FIG. 2 shows a further embodiment of the method, in which a slightly modified method-related set-up has been placed in a guide funnel 8. In the method-related set-up shown in FIG. 2, the positioning form 7 is formed in the upper casing part 2 so that the object 3 is at first arranged on the joint surface 4 of the lower casing part 1 in order to be precisely aligned by the positioning form 7 when the upper casing part 2 is made to approach the lower casing part 1. The guide funnel 8 prevents lateral drifting off of the casing parts 1, 2 or of the object 3 during the fusing process because the clearances of said guide funnel 8 very precisely match the external dimensions of the casing parts. After the continuous formed body comprising the casing parts 1, 2 and the object 3 has been placed in the guide funnel 8, two plunger elements 9 move into the guide funnel 8 and subject the first and second casing parts 1, 2 to pressure force. Subsequently, with the pressure maintained unchanged, a temperature is generated which causes the material of the casing parts 1, 2 to melt. As a result of the pressure and the temperature, the two casing parts 1, 2 fuse and enclose the object 3.

In order to prevent air bubbles in the seam from arising in the soft, melted material of the casing parts 1, 2 during the pressing and fusing procedure, in a further exemplary embodiment a vacuum can be generated, either before or during the joining process, so that any air or air bubbles can be removed. In this way, in addition, it is possible to reduce stress in the seam because the presence of air inclusions can be prevented, which air inclusions would otherwise lead to forced stress.

In a further exemplary embodiment the casing parts 1, 2 and/or the object 3 can be designed so as to be rotationally symmetrical. In this way a volume symmetry relating to the first joint surface 4 and/or to the second joint surface 5 can be produced so that the volume fractions are identical. In this way a constant hydrostatic pressure along the seam arises during the pressure phase and fusing phase so that no transverse forces arise as a result of the pressure being exerted, which transverse forces could otherwise, during the process of joining, cause the object 3 to move out of its defined position.

Figure 3:
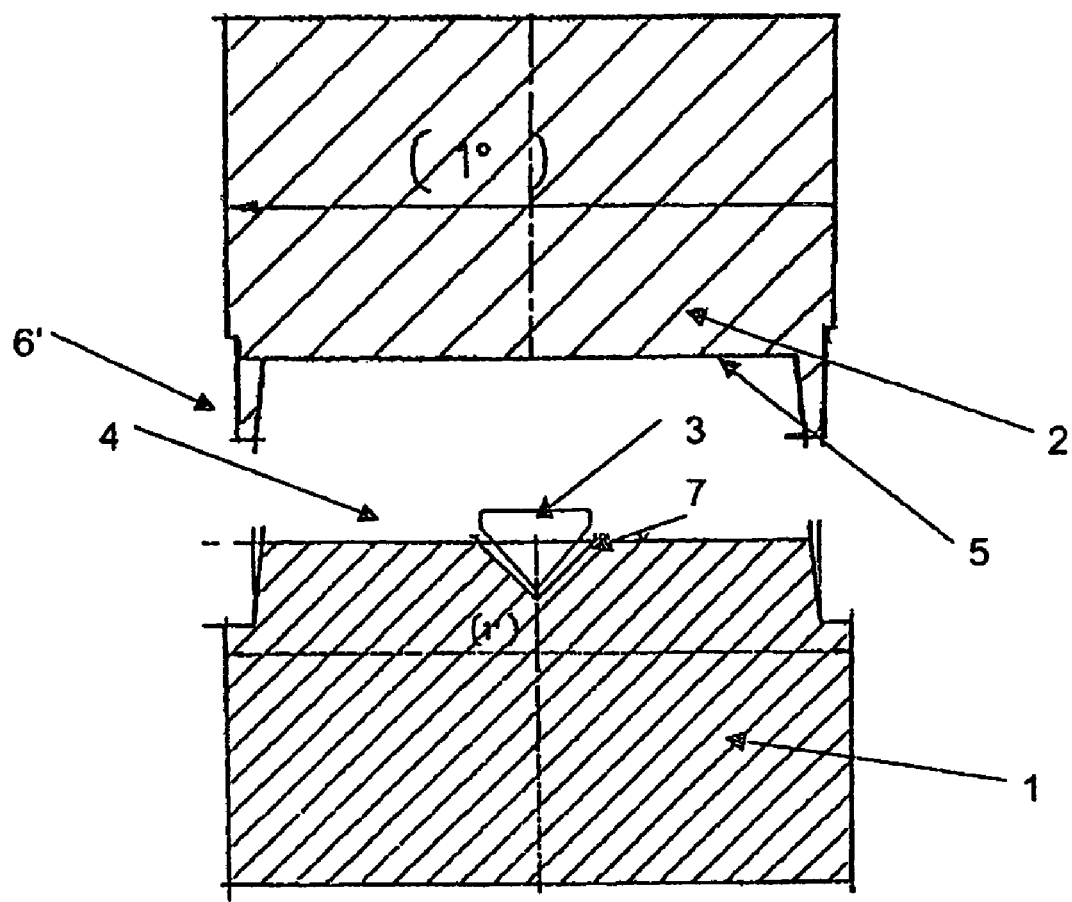
FIG. 3 a further exemplary diagrammatic view of the first and second casing parts.

FIG. 3 shows a further diagrammatic view of the first and the second casing parts 1, 2. In this diagram the object 3 has been placed in the positioning form 7 in the first joint surface 4 of the first casing part 1. Furthermore, the elevation of the first casing part 1 is of a conical design, as is the rim 6' of the second casing part 2, so that a press fit or form closure can be achieved that causes the first and the second casing parts to remain in their brought-together position, thus making possible easier handling of the casing bodies as well as more precise positioning.

Figure 4:
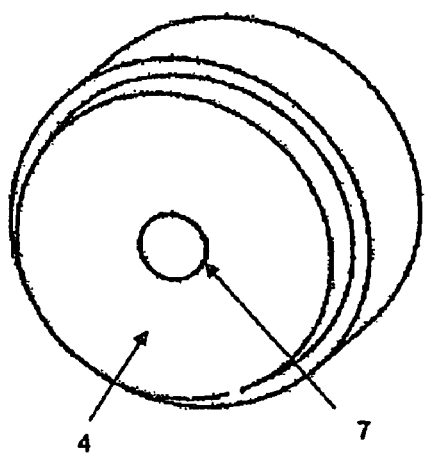
FIGS. 4 and 5 three-dimensional exemplary views of a first and a second casing part.

FIG. 4 shows a three-dimensional view of the first casing part with a first joint surface 4, in which a positioning form 7 of the object is provided.

Figure 5:
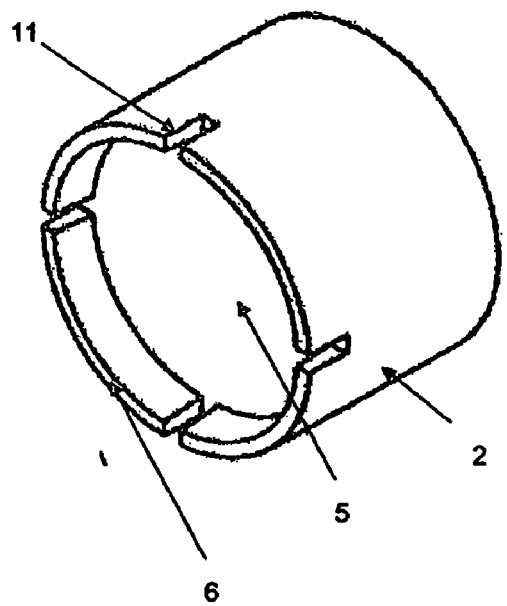

FIG. 5 shows a three-dimensional view of the second casing part, whose rim 6 comprises openings through which any air that is present during the pressing and melting process can escape.

Figure 6:
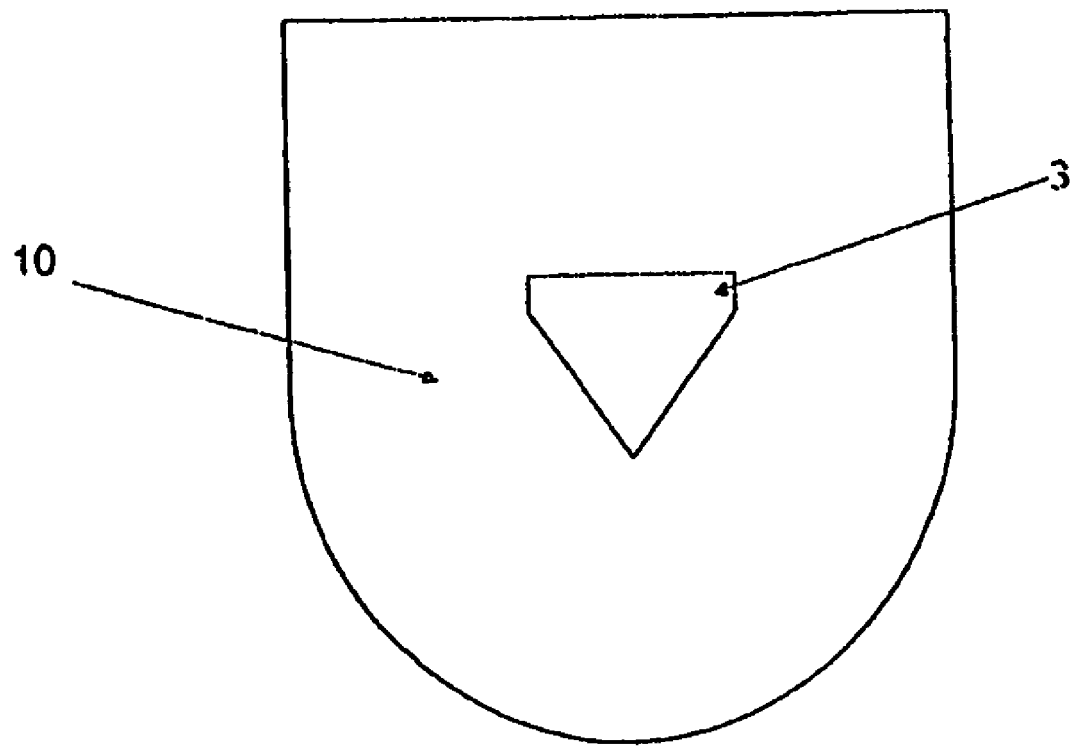
FIG. 6 an exemplary diagrammatic view of an end product from the production method.

FIG. 6 diagrammatically shows a product produced by means of the method according to the invention. In this arrangement a single-part body 10, which has arisen after melting and pressing, comprises an object 3, for example a diamond. Following the process of pressing and melting, the body 10 that has been produced from the casing parts 1, 2 is processed, for example rotary processed and/or polished, such that a particular visual effect, for example a magnification effect or a diminution effect, is produced by means of a particular geometry and surface treatment, for example lathe processing and/or polishing. For example, in the exemplary embodiment shown in FIG. 6 one of the casing parts has been ground to a dome shape, which due to light refraction effects makes the object 3 appear larger from the outside.

Instead of positioning the object 3 in relation to the external contour of the body 10 in that the object is placed so as to be centred in a defined position on a joint surface 4, 5, this can also take place by subsequent treatment which causes material of the body 10 to be removed from around the object 3 such that said object 3 is subsequently located at a defined position in relation to the external contour of the body 10.

In addition, it should be pointed out that "comprising" does not exclude other elements or steps, and "a" or "one" does not exclude a plural number. Furthermore, it should be pointed out that characteristics or steps which have been described with reference to one of the above exemplary embodiments can also be used in combination with other characteristics or steps of other exemplary embodiments described above. Reference characters in the claims are not to be interpreted as limitations.

The invention claimed is:

1. A production method for incorporating an object into a multi-part casing that is at least in part transparent, comprising:
   providing a first plastic casing part with a first joint surface and positioning form;
   providing a second plastic casing part with a second joint surface;
   diamond polishing at least one of the first and second joint surfaces to form a planar, transparent, and mirror-finish surface;
   inserting the first casing part, the second casing part, and the object into a hot vacuum press so that the first and second joint surfaces face one another and so that the object is aligned within the positioning form;
   bringing the first and second joint surfaces together within the press while the object remains aligned within the positioning form and between the first and second joint surfaces;
   fusing the first and second joint surfaces within the press by subjecting the joint surfaces to a pressure force and to an elevated temperature so that the first casing part on the first joint surface makes a transition to the second casing part on the second joint surface devoid of a visible seam; and
   providing a vacuum before or during fusing to prevent air inclusions from arising between the first and second casing parts, wherein one of the first and second casing parts comprises a rim that is circumferential at least in some sections,
   wherein the other of the first and second casing parts comprises an elevation, and
   wherein the first and second casing parts are brought together so that the rim engages the elevation with a positive fit.

2. The production method according to claim 1, wherein the press comprises a guide funnel, and wherein the first casing part, the second casing part, and the object are inserted in the guide funnel.

3. The production method according to claim 2, wherein the press comprises at least one plunger element, and wherein the pressure force is generated by moving the at least one plunger element into the guide funnel.

4. The production method according to claim 3, wherein the object comprises a surface that is aligned at a right angle to a wall surface of the guide funnel.

5. The production method according to claim 3, wherein the plunger element generates the pressure force parallel in relation to the wall surface of the guide funnel.

6. The production method according to claim 1, wherein a positioning form aligns the object for temporarily positioning the object, the object being centered in the first casing part or in the second casing part.

7. The production method according to claim 1, further comprising:
   centering the object on the first joint surface or on the second joint surface;
   wherein the object is configured to be rotationally symmetrical.

8. The production method according to claim 6, wherein the object is positioned in a volume-symmetrical manner in a radial direction in relation to the first joint surface of the first casing part, and in relation to the second joint surface of the second casing part.

9. The production method according to claim 1, further comprising:
   producing a visual effect in at least one of the first casing surface of the first casing part and the second casing surface of the second casing part.

10. The production method according to claim 1, further comprising:
    producing the first casing part and the second casing part by at least one of an injection molding method and lathe processing.

11. The production method according to claim 1, wherein at least one of the elements comprising the rim or the elevation is conically shaped.

12. The production method according to claim 1, wherein the rim comprises openings for pulling the vacuum.

13. The production method according to claim 1, wherein during fusing, the first casing part and the second casing part are heated such that they assume a pasty state.

* * * * *